United States Patent [19]
Deshaies et al.

[11] Patent Number: 6,165,731
[45] Date of Patent: Dec. 26, 2000

[54] ASSAY FOR THE UBIQUITINATION-PROMOTING ACTIVITY OF HUMAN PROTEINS

[75] Inventors: Raymond Deshaies, Claremont; Svetlana Lyapina, South Pasadena; Craig C. Correll, Pasadena, all of Calif.

[73] Assignee: California Institute of Technology, Pasadena, Calif.

[21] Appl. No.: 09/235,572

[22] Filed: Jan. 22, 1999

Related U.S. Application Data

[60] Provisional application No. 60/072,209, Jan. 22, 1998, and provisional application No. 60/083,447, Apr. 29, 1998.

[51] Int. Cl.[7] .................. G01N 33/53; G01N 33/573; C12P 13/18; A61K 39/395; C07K 16/00

[52] U.S. Cl. ................. 435/7.1; 435/6; 435/7.4; 435/7.9; 435/193; 435/252.3; 424/141.1; 536/23.2; 536/26.31; 536/26.32; 536/23.5; 530/387.9

[58] Field of Search .................. 435/7.1, 7.4, 7.9, 435/6, 193, 252.3; 424/141.1; 536/23.2, 24.31–32, 23.5; 530/387.9

[56] References Cited

PUBLICATIONS

Renny Feldman et al; A Complex of CDC4P, SKP1PAND CDC53P/Cullin Catalyzes Ubiquitination of the Phosphorylated CDK Inhibitor SIC1P; Cell, 91; 221–230, 1997.

*Primary Examiner*—Nita Minnifield
*Assistant Examiner*—Padma Baskar
*Attorney, Agent, or Firm*—Gray Cary Ware & Freidenrich LLP; Lisa A. Haile

[57] ABSTRACT

A method is provided for identifying a compound that affects an activity of a polypeptide subunit of a SCF complex. The method includes contacting a sample comprising a chimeric SCF complex assembled from subunits derived from *Saccharomyces cerevisiae* or human and another species and a CDC34p polypeptide with the compound under conditions that allow the components to interact, and adding to these components an E1 enzyme, ubiquitin and ATP, and a SCF substrate. The ubiquitination of the SCF substrate is measured. A chimeric in vitro assay system is provided for measuring CDC53p or CUL1p activity, comprising a CDC4p, CDC34p, and a SKP1p polypeptide, and either a CDC53p or CUL1p polypeptide. In this assay the CDC4p, CDC34p, and SKP1p polypeptide are either a yeast polypeptide or a polypeptide from another species, and at least one of the CDC4p, CDC34p, and SKP1p polypeptides is a yeast polypeptide and at least one of the CDC4p, CDC34p, and SKP1p polypeptides is a polypeptide from another species. A method is further provided for identifying a compound that affects the ability of a CDC4p, a SKP1p, a CDC34p, and a CDC53p or a CUL1p to ubiquitinate a substrate. The method includes contacting a sample comprising a CDC4p, a SKP1p, a CDC34p, and a CDC53p or CUL1p, with the compound under conditions sufficient to allow the components to interact, and adding to these components an E1 enzyme, ubiquitin and ATP, and a substrate for ubiquitination. The ability of the CDC4p, the SKP1p, the CDC34p, and the CDC53p or CUL1p, to ubiquitinate the substrate is measured. A method is also provided of identifying a polypeptide having a function of a CDC4 subunit of SCF. A method is further provided for identifying a polypeptide as a substrate for a ubiquitination reaction.

25 Claims, No Drawings

ASSAY FOR THE UBIQUITINATION-PROMOTING ACTIVITY OF HUMAN PROTEINS

CROSS REFERENCE TO RELATED APPLICATIONS

This application claims the benefit of the U.S. Provisional Application Nos. 60/072,209, filed on Jan. 22, 1998 and Ser. No. 60/083,447, filed Apr. 29, 1998 which are incorporated herein by reference.

STATEMENT AS TO FEDERALLY SPONSORED RESEARCH

This invention was made with Government support under Grant No. GM 52466-01 awarded by the USPHS. The Government has certain rights in this invention.

FIELD OF THE INVENTION

This invention relates generally to the field of cell cycle control and more specifically to the role of ubiquitination in the regulation of cell cycle progression.

BACKGROUND OF THE INVENTION

The irreversible nature of proteolysis makes it well-suited to serve as a regulatory switch for controlling unidirectional processes. This principle is evident in the control of the cell cycle, where initiation of DNA replication, chromosome segregation, and exit from mitosis are triggered by the destruction of key regulatory proteins (Schwob et al., *Cell* 79:233–244, 1994; Glotzer et al., *Nature* 349:132–138, 1991; Cohen-Fix, et al., *Genes Dev.* 10:3081–3093, 1996). Proteins are typically marked for proteolytic degradation by attachment of multiubiquitin chains.

In the early 1970s a novel protein was extracted from bovine thymus which was thought to have properties relating to the differentiation of T and B lymphocytes. This same protein was later found to be not only in the thymus but in all other eukaryotic cells. Due to its ubiquitous nature, the new protein was named "ubiquitous immunopoietic polypeptide" (Goldstein et al., *Proc. Natl. Acad. Sci. U.S.A.* 72: 11–15, 1975). Another protein of similar molecular weight was also discovered, and seemed to be involved in the ATP dependant degradation of denatured globulin in reticulocytes (Ciechanover et al., *Biochem. Biophys. Res. Commun.* 81,1100–1105, 1978).

This protein was a small protein made up of only 76 amino acids, and is now known as ubiquitin. Ubiquitin has many diverse functions, and is one of the most highly conserved sequences of all proteins found in eukaryotic cells, with only minor variations of two or three amino acids found between organisms as evolutionarily dissimilar as mammals, oats and yeasts (Özkaynak et al., *EMBO J.* 6(5):1429–1439, 1987).

Ubiquitin may have many roles in cell function including the mediation of various stress responses, repair of damaged DNA, regulation of differential gene expression, modification of histones and receptors, effects in neurodegenerative diseases, and control of the cell cycle. Other novel functions also suggested include the behavior of ubiquitin in a 'chaperone-like' role in the assembly of ribosomal proteins and as a response to heat shock. However, the most important role appears to be the role ubiquitin plays in selective protein degradation. The ability of ubiquitin to target proteins for degradation gives it a key role in the regulation of the cell cycle.

Many of the enzymes involved in ubiquitin dependant proteolysis have been identified, and the mechanism by which certain proteins are degraded has been determined. The presence of at least two different components required for ubiquitin dependant proteolysis have been confirmed, and that the mechanism of degradation is known to require the utilization of energy obtained from ATP (Ciechanover et al., *Proc. Natl. Acad. Sci. U.S.A.* 77:1365–1368, 1980).

The first step in selective degradation is the ligation of one or more ubiquitin molecules to a protein substrate (Hershko et al., *Proc. Natl. Acad. Sci. U.S.A.* 77:1783–1786, 1980). This process is initiated by ubiquitin-activating enzyme (E1), which activates ubiquitin by adenylation and becomes linked to it via a thiolester bond. Ubiquitin is then transferred to a ubiquitin-conjugating enzyme, E2. Whereas E2s can directly attach ubiquitin to lysine residues in a substrate, most physiological ubiquitination reactions probably require a ubiquitin ligase, or E3 (Hershko et al., *J. Biol. Chem.* 258:8206–8214, 1983). E3s have been implicated in substrate recognition and, in one case, transfer of ubiquitin from E2 to a substrate via an E3~ubiquitin-thiolester intermediate (Scheffner et al., *Nature* 373:81–83, 1995). Once the substrate is multiubiquitinated, it is then recognized and degraded by the 26S proteasome.

A novel ubiquitination pathway has recently been discovered in budding yeast. Components of this pathway include the CDC53, CDC4, and SKP1 gene products, which assemble into a ubiquitin ligase complex known as $SCF^{CDC4}$ (for $\underline{S}$KP1, $\underline{C}$ullin, $\underline{F}$-box protein CDC4). In yeast, SCF collaborates with the E2 enzyme CDC34 to catalyze ubiquitination of the CDK inhibitor SIC1. The specificity of SCF is thought to be governed by SKP1 and the F-box-containing subunit CDC4, which together form a substrate receptor that tethers SIC1 to the complex. The assembly of this receptor is thought to be mediated by a direct interaction between yeast SKP1 and the F-box domain of CDC4 (Feldman et al., *Cell* 91:221–230, 1997; Skowyra et al., *Cell* 91:209–219, 1997).

Whereas genetic analysis has revealed that SIC1 proteolysis requires CDC4, G1 cyclin proteolysis depends upon a distinct F-box-containing protein known as GRR1 (Barral et al., *Genes Dev.* 9:399–409, 1995). Alternative SCF complexes ($SCF^{GRR1}$) assembled with GRR1 instead of CDC4 bind G1 cyclins but not SIC1, suggesting that there exist multiple SCF complexes in yeast whose substrate specificities are dictated by the identity of the F-box subunit.

Components of the SCF ubiquitination pathway have been highly conserved during evolution. Human homologues of the yeast CDC34 and SKP1 have been reported (Plon et al., *Proc. Natl. Acad. Sci. USA* 90:10484–10488, 1993; Zhang et al., *Cell* 82:912–925, 1995), and F-box-containing proteins like CDC4 and GRR1 have been identified in many eukaryotes (Bai et al., *Cell* 86:263–274, 1996). Many of these F-box proteins also contain either WD-40 repeats (like CDC4) or leucine-rich repeats (like GRR1). A potential human counterpart of GRR1, SKP2, has been identified along with human SKP1 as a Cyclin A/CDK2-associated protein that is necessary for S-phase progression (Zhang et al., *Cell* 82:912–925, 1995). Homologues of CDC53, which are known as Cullins, are also present in many eukaryotes, including humans and nematodes (Kipreos et al., *Cell* 85:1–20, 1996; Mathias et al., *Mol. Cell. Biol.* 16:6634–6643, 1996).

It is currently thought that transitions from one phase of the cell cycle to another are coupled to fluctuations in the activity of a family of cyclin-dependent protein kinases (CDKs). These kinases represent a special family of kinases that are activated by regulatory proteins known as cyclins. Cyclins bind to the catalytic kinase subunit and trigger a battery of post-translational modifications that culminate in the activation of the kinase. Eventually, the kinase activity is extinguished by proteolysis of the stimulatory cyclin subunit. In yeast, a crucial means of regulating cell cycle progression is by the targeted degradation of both activating and inhibitory subunits of the cyclin dependent kinase Cdc28. The G1 to S phase transition is driven by the destruction of an inhibitor (SIC1p) that restrains the activity of a cyclin/CDK complex that triggers DNA replication. The ubiquitin conjugating enzyme CDC34 has been implicated in the ubiquitination of the regulatory proteins and the ultimate the destruction of them (Goebl et al., *Science* 241:1331–5, 1988).

The two other proteins in the SCF complex, CDC4 and CDC53, have been found to be required for the G1 to S phase transition. The absence of functional CDC4, CDC34 or CDC53 from the cell gives rise to identical terminal morphologies suggesting that these proteins interact to perform a function. Numerous genetic interactions are seen between these genes and the encoded proteins are found physically associated in vivo. Thus, the G1 to S phase transition in the yeast cell cycle requires the activity of a complex containing CDC4, CDC34 and CDC53. Identification of counterparts of CDC4, CDC34, and CDC53 in other species such as humans will provide new insights into how disturbances in ubiquitination influence diseases associated with cell proliferation.

Several human cell cycle regulators are targeted for ubiquitination following their phosphorylation by CDKs, implicating them as potential substrates of SCF pathway(s) in human cells. Among them is the CDK inhibitor p27, the abundance of which may be regulated by CDC34-dependent ubiquitination (Pagano et al., *Science* 269:682–685, 1995; Sheaff, R. J., et al., *Genes Dev.* 11:1464–1478, 1997). In addition, Cyclins E and D1 are degraded by a ubiquitin-dependent pathway following phosphorylation at a specific site (e.g., Won & Reed, *EMBO J.* 15:4182–4193, 1996). It has also been suggested that cyclin A is a target of an SCF pathway. Alternatively, SCF-bound Cyclin A/CDK2 may phosphorylate SCF subunits or potential substrates such as E2F-1/DP-1, thereby activating SCF-dependent ubiquitination (Dynlacht et al., *Genes Dev.* 8:1772–1786, 1994).

Ubiquitination is also thought to play a role in tumor formation, as the ubiquitin system is associated with cell cycle regulation (King, R. W., et al., *Science*, 274:1652–9, 1996). For example, the protein E6, encoded by the human papilloma virus, which causes cervical cancer, was found to bind to a human ubiquitin-protein ligase, thereby targeting the tumor suppressor p53 for ubiquitin-mediated degradation (Scheffner et al., *Cell* 63:1129–36, 1990; Huibregtse et al., *Molecular and Cellular Biology* 13:775–84, 1993).

SUMMARY OF THE INVENTION

The present invention is based on the discovery of an assay for detecting the activity of the yeast polypeptides, CDC4p, CDC53p, SKP1p, and CDC34p, and their human counterparts. This assay allows detection of compounds that affect ubiquitination and thus, cell cycle regulation in cells.

A method is provided for identifying a compound that affects an activity of a polypeptide subunit of a SCF complex. The method includes contacting a sample including a chimeric SCF complex assembled from subunits derived from *Saccharomyces cerevisae* or human and another species, and a CDC34p polypeptide, with the compound under conditions that allow the components to interact, and adding to these components an E1 enzyme, ubiquitin and ATP, and a SCF substrate. The ubiquitination of the SCF substrate is measured and compared to the level of ubiquitination of the SCF substrate in a sample not contacted with the compound. The level of ubiquitination of the SCF substrate indicates the effect of the compound on the polypeptide subunit.

A chimeric in vitro assay system is provided for measuring CDC53p or CUL1p activity, comprising a CDC4p, CDC34p, and a SKP1p polypeptide, and either a CDC53p or CUL1p polypeptide. In this assay the CDC4p, CDC34p, and SKP1p polypeptide are either a yeast polypeptide or a polypeptide from another organism, wherein at least one of the CDC4p, CDC34p, and SKP1p polypeptides is a yeast or human polypeptide and at least one of the CDC4p, CDC34p, and SKP1p polypeptides is a polypeptide from another species.

A method is provided for identifying a compound that affects the ability of a CDC4p, a SKP1p, a CDC34p, and a CDC53p or a CUL1p to ubiquitinate a substrate. The method includes contacting a sample comprising a CDC4p, a SKP1p, a CDC34p, and a CDC53p or CUL1p, with the compound under conditions sufficient to allow the components to interact, and adding to these components an E1 enzyme, ubiquitin and ATP, and a substrate for ubiquitination. The ability of the CDC4p, the SKP1p, the CDC34p, and the CDC53p or CUL1p, to ubiquitinate the substrate is measured and compared to the level of ubiquitination of the substrate in a sample not contacted with the compound. In this method, the level of ubiquitination of the substrate indicates the effect of the compound on the CDC4p, the SKP1p, the CDC34p, and the CDC53p or the CUL1p.

A method is provided for identifying a polypeptide having a function of a CDC4 subunit of SCF. The method includes incubating a test polypeptide with a SKP1p, a CDC53 or a CUL1p, and a CDC34p, an E1 enzyme, a ubiquitin, ATP and a substrate under conditions sufficient for the polypeptides to interact, and measuring the ability of the test polypeptide, the SKP1p, the CDC53 or the CUL1p, the CDC34p, and the E1 enzyme and the CDC34p to attach ubiquitin to the substrate.

A method is also provided for identifying a polypeptide as a substrate for ubiquitination, including incubating a test polypeptide with a SCF complex, CDC34p, ubiquitin, ATP and E1 under conditions sufficient for the polypeptides to interact; and measuring the ability of the SCF to attach ubiquitin to the test polypeptide.

DESCRIPTION OF THE PREFERRED EMBODIMENTS

The present invention relates to the role of ubiquitination and a biochemical assay to monitor the activities of CDC34p, CDC53p, and SKP1p. These methods and assays are useful in the detection of agents that modulate the activities of these polypeptides in ubiquitination, and the identification of novel substrates of the ubiquitin pathway.

It must be noted that as used herein and in the appended claims, the singular forms "a," "and," and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

Unless defined otherwise, all technical and scientific terms used herein have the same meaning as commonly understood to one of ordinary skill in the art to which this invention belongs. Although any polypeptides, compounds and materials similar or equivalent to those described herein can be used in the practice or testing of the invention, the preferred methods, devices and materials are now described.

All publications mentioned herein are incorporated herein by reference in full for the purpose of describing and disclosing the cell lines, antibodies, and methodologies which are described in the publications which might be used in connection with the presently described invention. The publications discussed above and throughout the text are provided for their disclosure prior to the filing date of the present application.

In one embodiment, a chimeric in vitro assay system is provided for CDC53p or CUL1p activity. This assay system includes a CDC4p, CDC34p, and a SKP1p polypeptide, and either a CDC53p or CULp polypeptide, such as a CUL1p polypeptide. In this assay system the CDC4p, CDC34p, and SKP1p polypeptide are either a yeast polypeptide or a polypeptide from another species. In the assay system, at least one of the CDC4p, CDC34p, and SKP1p polypeptides is a yeast or a human polypeptide and at least one of the CDC4p, CDC34p, and SKP1p polypeptides is a polypeptide from a species other than yeast or human, respectively. In one embodiment, the species is a mammalian species. In another embodiment, the mammalian species is human.

CDC4, CDC53, SKP1, and CDC34 have been identified in *Saccharomyces cerevisiae* as being essential for cell cycle progression. In yeast, CDC4, CDC34, CDC53, and SKP1 have been cloned and mapped. "Yeast" includes members of the species *Saccharomyces cerevisiae* or any other yeast species. The phrase "another species" refers to members of all other heterologous species, including mammals. In one embodiment, "another species" is a mammalian species. Thus, when a *Saccharomyces cerevisiae* polypeptide is utilized, "another species" is any other species than *Saccharomyces cerevisiae* or other yeast, and when human polypeptide is utilized, "another species" is any other species than human but could include yeast. "CDC4" refers to a gene encoding a polypeptide (CDC4p) which in yeast is involved in the initiation of DNA synthesis and spindle pole body separation, dispensable for both mitotic and meiotic spindle pole body duplication. CDC4p is part of the ubiquitin ligase complex (Yochem and Byers, *J. Mol. Biol.* 195, 233–245, 1987). "CDC53" refers to a gene encoding a polypeptide (CDC53p) that acts with CDC4p and CDC34p to control the G1-S phase transition. CDC53p activates the hydrolysis of an E2-ubiquitin and enables the ubiquitination of a substrate. Thus, CDC53p assists in mediating the proteolysis of the CDK inhibitor SIC1p in late G1 (Mathias, N., et al., Mol. Cell Biol. 16:6634–6643). The "CUL polypeptides" are human polypeptides related to CDC53 that can activate the hydrolysis of an E2-ubiquitin and enable the ubiquitination of a substrate (Kipreos et al., *Cell* 85:1–20, herein incorporated by reference). The CUL genes encode the polypeptides CUL1p, CUL2p, CUL3p, CUL4ap, CUL4 bp, and CUL5p. As demonstrated herein, a CUL polypeptide (CUL1p, see Examples below) can form an SCF complex with CDC4p and SKP1p. "CDC34" refers to a gene encoding CDC34p, a ubiquitin-conjugating enzyme. The human CDC34 has been cloned (Plon et al., Proc. Natl. Acad. Sci. USA 90:10484–10488, herein incorporated by reference). "SKP1" refers to a gene encoding SKP1p polypeptide, a 29 Kd kinetochore protein subunit of CBF3, a multiprotein complex which binds to an element of centromeres. The human SKP1 has been cloned (Zhang et al., *Cell* 82: 912–925, 1995, herein incorporated by reference and may act as a subunit of CBF3).

In yeast, CDC4p, CDC53p and SKP1p assemble into a complex designated "SCF" (Feldman et al., *Cell* 91:221–230, 1997; Skowyra et al., *Cell* 91:212–219, 1997, both herein incorporated by reference). A "chimeric SCF complex" includes polypeptides from more than one organism or species. In one embodiment, a chimeric SCF complex includes polypeptides from *Saccharomyces cerevisiae* or other yeast and from another organism such as human, murine or other heteroglogous species. As demonstrated herein, CDC53p can be replaced by a polypeptide encoded by a CUL gene. In one embodiment, the CDC53p of the SKF complex is replaced by CUL1p. In one embodiment, yeast CDC4p, human CUL1p, and yeast SKP1p are subunits which form an SCF complex. An SCF complex directs the ubiquitination of a polypeptides (SCF substrates), including but not limited to SIC1p. "Ubiquitination" refers to the attachment of ubiquitin to a polypeptide. An "SCF substrate" is a polypeptide whose ubiquitination is promoted by SCF. An example of an SCF substrate is SIC1p. "SIC1p" refers to a polypeptide encoded by the SIC1 gene, which has been cloned and sequenced. In yeast, SIC1p is involved in the release from glucose repression, invertase expression, and sporulation (Celenza, et al., Mol. Cell Biol. 9:5045–5054; Nugroho et al. *Mol. Cell Biol.* 3320–8, 1994). CDC4p, CDC34p, CDC53p, and SKP1p promote DNA replication by attaching ubiquitin to SIC1p. The ubiquitinated SIC1p is then targeted for degradation by a ubiquitin dependent protease. The substrate of the SCF complex may be a chimeric protein, such as a chimeric SIC1p (see below).

As used in connection with the present invention the term "polypeptide" refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" as used herein is intended to encompass any amino acid sequence and include modified sequences such as glycoproteins. The term "polypeptide" is specifically intended to cover naturally occurring proteins, as well as those which are recombinantly or synthetically synthesized. "Fragments" are a portion of a protein. Fragments can have the same or substantially the same amino acid sequence as the naturally occurring protein. "Substantially the same" means that an amino acid sequence is largely, but not entirely, the same, but retains a functional activity of the sequence to which it is related, for example, the fragment may bind to an antibody that also recognizes the full length polypeptide. In general two amino acid sequences are substantially the same" or "substantially homologous" if they are at least 85% identical.

The term "substantially purified" as used herein refers to a polypeptide which is substantially free of other proteins, lipids, carbohydrates or other materials with which it is naturally associated. In one embodiment the substantially purified polypeptide comprises at least 80% dry weight, preferably 95–99% dry weight of a polypeptide of interest. One skilled in the art can purify polypeptides such as CDC4p, CDC53p, CDC34p, SKP1p, and SIC1p using standard techniques for protein purification. The substantially pure polypeptide will yield a single major band on a non-reducing polyacrylamide gel. The purity of the polypeptide can also be determined by amino-terminal amino acid sequence analysis.

As used herein, the term "functional polypeptide" refers to a polypeptide which possesses biological function or activity which is identified through a defined functional assay and which is associated with a particular biologic, morphologic, or phenotypic alteration in the cell. The term "functional fragments of a polypeptide," refers to all fragments of a the polypeptide that retain an activity of the polypeptide. In one specific, nonlimiting example a functional fragment of CDC4p, CDC53p, or SKP1p retains the ability to function as part of an SCF complex and thereby ubiquitinate SIC1p. Biologically functional fragments, for example, can vary in size from a polypeptide fragment as small as an epitope capable of binding an antibody molecule to a large polypeptide capable of participating in the characteristic induction or programming of phenotypic changes within a cell.

Minor modifications of the primary amino acid sequences of a polypeptide may result in polypeptide which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the polypeptide still exists. Further, deletion of one or more amino acids can also result in a modification of the structure of the resultant molecule without significantly altering its activity. Deletion can lead to the development of a smaller active molecule which could have broader utility. For example, it may be possible to remove amino or carboxy terminal amino acids and retain an activity of a CDC4p, CDC53p, SKP1p, or an SIC1p polypeptide.

The method and assay systems of the invention include CDC4p, CDC53p (or CULp), SKP1p and SIC1p polypeptides that are substantially the same as those polypeptides known in the art. A substantially the same CDC4p, CDC53p (or CULp), SKP1p and SIC1p polypeptides refers to amino acid sequences that retain the activity of a polypeptide as described herein, e.g., the ability to function in or in combination with an SCF complex. The polypeptides of the invention include conservative variations of the CDC4p, CDC53p, CULp, SKP1p and SIC1p polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

A method of identifying an compound that affects an activity of a polypeptide subunit of a SCF complex is also provided. This method includes contacting a sample containing a combination of subunits of a SCF complex from yeast and another species and a CDC34p polypeptide with the compound under conditions that allow the components to interact, and adding an E1 enzyme, ubiquitin, adenosine 5'-triphosphate (ATP), and a SCF substrate. The ubiquitination of the SCF substrate is measured and compared to the ubiquitination of the SCF substrate in a sample not contacted with the compound. An "SCF substrate" is any substrate that is ubiquitinated by an SCF complex. An "E1 enzyme" is an enzyme involved in the activating ubiquitin. The E1 enzyme is well known to one of skill in the art (e.g., Hershko et al., Ann. Rev. Biochem. 61:761–807, 1992, and Monia et al., Biotechnol. 8: 209–215, 1990, herein incorporated by reference). In this method, the level of ubiquitination of the SCF substrate is indicative of the effect of the compound on the polypeptide subunits.

A compound can affect the activity of a polypeptide subunit of a SCF complex by either stimulating or inhibiting the ubiquitination of the SCF substrate. A compound "inhibits" ubiquitination if the level of the substrate that is ubiquitinated is decreased as compared with the level of substrate ubiquitinated in the absence of the test compound. In one embodiment, the compound inhibits ubiquitination by 50% or more as compared to a control sample not contacted with the compound. A compound "stimulates" ubiquitination if the fraction of the substrate that is ubiquitinated or the amount of ubiquitin incorporated into substrate is increased as compared to reactions performed in the absence of the test compound. In one embodiment, the compound stimulates ubiquitination by 50% or more as compared to a control sample not contacted with the compound.

The phrase "compound that affects an activity of a polypeptide subunit of a SCF complex" denotes derivatives of antibodies, peptides, chemical compounds or pharmaceuticals that affect an activity of SCF. Without being bound by theory, the compound can affect the association of the CDC4p, CDC53p, and SKP1p, can interfere with an activity of CDC4p, CDC53p, or SKP1p, can interfere with the interaction of SCF with an SCF substrate, or can interfere with the process of ubquitinating the substrate, for example. The term includes both biologic agents and chemical compounds. The determination and isolation of compounds is well described in the art. (See, e.g., Lerner, Trends NeuroSci. 17:142–146, 1994, which is hereby incorporated in its entirety by reference.) "Incubating" includes conditions which allow contact between the test composition and the SCF complex. Contacting includes in solution and in solid phase.

The test compound may optionally be a combinatorial library for screening a plurality of compositions. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229–237, 1988).

Any of a variety of procedures may be used to clone the genes of use with the method of the present invention when the test compound is in a combinatorial library or is expressed as a gene product (as opposed to a chemical compound). One such method entails analyzing a shuttle vector library of DNA inserts (derived from a cell which expresses the compound) for the presence of an insert which contains the composition gene. Such an analysis may be conducted by transfecting cells with the vector and then assaying for expression of the composition binding activity. The preferred method for cloning these genes entails determining the amino acid sequence of the composition protein. Usually this task will be accomplished by purifying the desired composition protein and analyzing it with automated sequencers. Alternatively, each protein may be fragmented as with cyanogen bromide, or with proteases such as papain, chymotrypsin or trypsin (Oike, Y., et al., J. Biol. Chem., 257:9751–9758, 1982; Liu, C., et al. Int. J. Pept. Protein Res., 21:209–215, 1983). Although it is possible to determine the entire amino acid sequence of these proteins, it is preferable to determine the sequence of peptide fragments of these molecules.

The compounds of the present invention can be extracted and purified from the culture media or a cell by using known protein purification techniques commonly employed, such as extraction, precipitation, ion exchange chromatography, affinity chromatography, gel filtration and the like. Compounds can be isolated by affinity chromatography using the modified receptor protein extracellular domain bound to a column matrix or by heparin chromatography.

Also included in the screening method of the invention is combinatorial chemistry methods for identifying chemical compounds that affects an activity of a polypeptide subunit of a SCF complex.

In one embodiment the compound is an antibody, or a biologically active fragment thereof, which interferes with or binds to a polypeptide in an SCF complex. The antibody can bind CUL1p, CDC53p, CDC4p, SKP1p. In another embodiment, the antibody may bind CDC34p.

CUL1p, CDC53p, CDC4p, SKP1p, or CDC34p polypeptides can be used to produce antibodies which are immunoreactive or bind to epitopes of the polypeptide of interest. Antibodies which consist essentially of pooled monoclonal antibodies with different epitopic specificities, as well as distinct monoclonal antibody preparations are included. The invention includes the use of commercially available monoclonal antibodies which recognize CUL1p, CDC53p, CDC4p, SKP1p, or CDC34p.

Polyclonal antibodies can also be used in the method of the invention. The preparation of polyclonal antibodies is well-known to those skilled in the art. See, for example, Green et al., "Production of Polyclonal Antisera," in: *Immunochemical Protocols*, pages 1–5, Manson, ed., Humana Press, 1992; Coligan et al., "Production of Polyclonal Antisera in Rabbits, Rats, Mice and Hamsters," in: *Current Protocols in Immunology*, section 2.4.1, 1992, which are hereby incorporated by reference.

The preparation of additional monoclonal antibodies likewise is conventional. See, for example, Kohler & Milstein, *Nature* 256:495, 1975; Coligan et al., sections 2.5.1–2.6.7; and Harlow et al., in: *Antibodies: a Laboratory Manual*, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)," in: *Methods in Molecular Biology*, Vol. 10, pages 79–104, Humana Press, 1992.

Alternatively, an antibody that binds CUL1p, CDC53p, CDC4p, SKP1p, or CDC34p may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl Acad. Sci. USA* 86:3833, 1989, which is hereby incorporated in its entirety by reference. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993, which are hereby incorporated by reference.

Antibodies of the invention also may be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994, which are hereby incorporated by reference. Cloning and expression vectors that are useful for producing a human immunoglobulin phage library can be obtained, for example, from STRATAGENE Cloning Systems (La Jolla, Calif.).

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind CUL1p, CDC53p, CDC4p, SKP1p, or CDC34p can be prepared using an intact polypeptide or fragments containing small peptides of interest as the immunizing antigen.

The effect of the compound on the activity of a polypeptide subunit of an SCF complex is measured by measuring the ubiquitination of an SCF substrate. Assays for ubiquitination are well known to one of skill in the art. In one embodiment, the ubiquitin used in the method of the invention is a derivatized ubiquitin. A "derivatized ubiquitin" is a ubiquitin molecule including a label that is readily identified. For example, the derivatized ubiquitin can be an $^{125}$I-ubiquitin, a fluorescent ubiquitin, a glutathione S-transferase conjugated ubiquitin and a biotinylated ubiquitin. Using assays well known in the art, the presence of the label, and thus the amount of derivatized ubiquitination, can be identified.

Ubiquitination results in an increase in the molecular weight of the substrate. Thus any assay which measures molecular weight of the substrate, such as SDS-poly acrylamide gel electrophoresis, can be used to measure ubiquitination. This assay can be readily adapted to the large scale screening of compound libraries by converting it to a solid phase format. In one specific nonlimiting example, ubiquitination assays can be performed with an appropriately engineered substrate in microtiter plate in the presence of a derivatized ubiquitin. For example, the ubiquitination of a chimeric substrate, such as a chimeric SIC1p can be measured. A "chimeric substrate" is a substrate for an enzymatic reaction comprised of two heterologous polypeptides.

Thus, in one embodiment, the chimeric SIC1p is a maltose binding protein SIC1p chimera containing a myc epitope-hexahistidine tag at the C-terminus (MBP-SIC1mycHis6p). Following the contacting of the components of the reaction, aliquots of the ubiquitination assays are transferred from a first microtiter plate to a second microtiter plate with an appropriate surface. In one embodiment, reactions are transferred to a microtiter plate whose wells have been coated with a reagent that can capture the substrate (e.g., for MBP-SIC1p, wells coated with amylose, anti-MBP antibody, anti-myc antibody, anti-SIC1p antibody, or NiNTA). After washing away unbound proteins, the substrate-coated wells can be directly imaged (e.g., for reactions performed with fluorescent or radiolabeled ubiquitin).

Alternatively, wells can be contacted with an appropriately reagent to capture derivitized ubiquitin (e.g., biotin-Ub, GST-Ub etc.) covalently linked to substrate MBP-SIC1mycHis6p. The wells would then be probed with reagents directed against the substrate (anti-MBP, anti-SIC1) to detect the extent of substrate-ubiquitin conjugates formed, or alternatively, a labeled substrate (fluorescent, radioactive) would be used and imaged directly. These assays are similar in design but yield distinct information, either of which can be used with the method of the invention. The first assay measures the total amount of ubiquitin incorporated into substrate, and the second measures the total fraction of substrate that becomes covalently linked to at least one ubiquitin molecule. Both of these assays can be used to differentiate between compounds that block the formation of the substrate-ubiquitin linkage versus those compounds that interfere with the elaboration of the substrate-linked polyubiquitin chains. All of the assays can be used to identify compounds that modulate the activities of an SKP1p, CUL1p, CDC34p, CDC4p, or SIC1p for example.

Another assay for ubiquitination is a scintillation proximity assay. This assay uses beads containing a fluor that emits light when activated by radioactive substances, and a means of conjugating the bead to ubiquitin. In one embodiment, the bead containing a fluorescent substrate is avidinated, and is contacted with biotinylated ubiquitin. A radiolabeled substrate, such as radiolabeled SIC1, is incubated with the beads in the presence of the reaction components. Ubiquitinated SIC1 is quantified by measuring bead fluorescence, which occurs only upon ubiquitination of the labeled SIC1. (See Bosworth, N. et al., Nature 341:167–168, 1989), incorporated herein by reference.)

In another embodiment, a method of identifying a polypeptide having a function of a CDC4p subunit of SCF is provided. This method includes incubating a test polypeptide with a SKP1p, a CDC53 or a CUL1p, and a CDC34p, an E1 enzyme, a ubiquitin, ATP and a substrate under conditions sufficient for the polypeptides to interact, and measuring the ability of the test polypeptide, the SKP1p, the CDC53 or the CUL1p, the CDC34p, the E1 enzyme and the CDC34p to attach ubiquitin to said substrate. The test polypeptide may contain an F-box. An "F-box" is a region of polypeptide which mediates an interaction between SKP1p (Feldman et al., Cell 91:221–230, 1997; Skowyra et al., Cell 91:209–219, 1997, herein incorporated by reference). F-box polypeptdides may also contain either WD-40 repeats (like CDC4) or leucine-rich repeats (like GRR1).

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

In the examples described below the letter "h" indicates the human form of the gene or protein and the letter "y" designates the yeast (e.g., Saccharomyces cerevisiae) form of the gene or protein. For example "hCDC4" indicates the human CDC4 gene and "yCDC34p" indicates the yeast CDC34 polypeptide.

Example 1

Materials and Methods

Yeast strains and reagents. Yeast strains, plasmids, and a HeLa cDNA library for the two-hybrid screen were a generous gift from R. Brent (Massachusetts General Hospital, Boston, Ma.). Wx131.2c cdc53-2$^{ts}$ strain was obtained from M. Goebl (Indiana University, Indianapolis, Ind.). Baculoviruses expressing hCDK2$^{HA}$, hCyclin A (D. Morgan, UCSF, San Francisco, Calif.), SKP2 (H. Zhang, Yale, New Haven, Conn.), hSKP1 (P. Sorger, MIT, Cambridge, Ma.) and plasmids pGEX-KG-hSKP1, pGEX-KG-SKP2 (P. Jackson, Stanford, Palo Alto, Calif.), pCS2+nβgal, pCS2+HA-SMC1 (S. Handeli, FHCRC, Seattle, Wash.) were kindly provided by the indicated investigators. Other baculoviruses were previously described (Feldman, R. M. R., et al. Cell 91:221–230, 1997). Ubiquitin and the Protein Biotinylation Kit were purchased from Sigma, and biotinylated ubiquitin was prepared according to the manufacturer's instructions. Ubiquitin aldehyde was a generous gift from R. Cohen (University of Iowa, Iowa City, Iowa).

Plasmid and baculovirus construction. Full length hCUL1 ORF was assembled from ESTs HE2 AB96 and HSVAD74 and subcloned into pRS316 and pMALc (New England Biolabs). The same hCUL1 fragment was also subcloned into pVL1393 (PharMingen) to generate an hCUL1-expressing baculovirus. An N-terminal epitope-tagged version of hCUL1 was constructed by inserting a DNA cassette that contains two tandem repeats of the Polyoma epitope (MEYMPME) followed by six histidine residues (designated as PHis6) into pRS316-hCUL1. $^{PHis6}$hCUL1 fragment was then subcloned into pFASTBAC1 (Gibco BRL) to generate a $^{PHis6}$hCUL1 baculovirus, and pDNA3.1/Zeo (Invitrogen) to generate pcDNA3.1-PHis6-hCUL1. pCS2+HA-hSKP1 was generated by subcloning a hSKP1 fragment from pGEX-KG-hSKP1 into pCS2+HA-SMC1.

Antibodies. Anti-hCUL1 antibodies were generated in rabbits immunized with either a fusion protein containing the first 41 residues of hCUL1 followed by GST (BAbCO), or a fusion protein containing GST followed by the last 86 residues of hCUL1 (Caltech antibody facility). Antibodies against hCUL1 and GST were affinity purified using MBP fusions of the corresponding peptides and GST, respectively, as described (Harlow, E., and Lane, D., *Antibodies: A Laboratory Manual*, Cold Spring Harbor Laboratory, Cold Spring Harbor, N.Y., 1988). Monoclonal anti-Polyoma antibodies were bound to protein A-Sepharose beads and cross-linked to protein A with dimethylpimilimadate (Harlow and Lane, 1988, supra) at a concentration of approximately 2 mg of antibodies per ml of protein A resin. Anti-HA resin was generated by coupling 1 ml of anti-HA ascites to 1 ml of CNBr activated agarose (Pharmacia Biotech) according to the manufacturer's protocol.

Expression and purification of proteins. Proteins expressed in bacteria or yeast were purified according to standard protocols and as described (Feldman, R. M. R., *Cell* 91:221–230, 1997). For the expression and purification of chimeric SCF complexes, Hi5 insect cells were infected with baculoviruses expressing $^{PHA}$CDC4 (PHA designates an epitope-tag consisting of two tandem repeats of the Polyoma epitope followed by three hemagglutinin epitopes), $^{CDC53pHA}$, $^{PHis6}$hCUL1 (MOIs of 6), ySKPF1$^{His6}$, or hSKP1 (MOIs of 4). Seventy-two hours postinfection, cells were collected and lysates were prepared as described (Feldman et al., 1997, supra). The Polyoma tagged proteins were affinity-purified from these lysates (Feldman et al., 1997, supra) to yield the various SCF complexes.

Cell cultures and transfections. WI-38 human lung fibroblasts were purchased from ATCC. HeLa S3 cells were a gift from S. Handeli (FHCRC, Seattle, Wash.). Cells were grown in DMEM-F12 (Gibco BRL) supplemented with 10% FBS (Gibco BRL) at 37°C./5%CO$_2$. Cells were transfected in 100 mm dishes by the modified calcium phosphate method (Chen, C., and Okayama, H., *Mol. Cell. Biol.* 7:2745–2752, 1987). 10 μg pCS2+HA-hSKP1 and 7.5 μg pcDNA3.1-PHis6-hCUL1 vectors were used per transfection plate. Transfection efficiency was monitored by cotransfection of 2.5 μg pCS2+nβgal plasmid per transfection plate followed by standard colorimetric gal assays (Sambrook, J., et al., *Molecular cloning: Assay for ☐-galactosidase in extracts of mammalian cells*, Cold Spring Harbor Laboratory Press, Cold Spring Harbor, N.Y., 1989). Total DNA concentration was 20 μg/100 mm dish and was adjusted for every transfection plate by adding empty vectors. Cells were harvested and lysed 24 hr posttransfection.

Immunoprecipitations and Western blotting. Baculovirus-infected insect cells were harvested and lysed at 48 hr (for Sf9 cells) or 72 hr (for Hi5 cells) postinfection in 0.8 ml of lysis buffer per 100 mm plate (as described in Feldman, R. M. R., et al. *Cell* 91:221–230, 1997). Metabolic labeling was done by incubating insect cells for 3 hr in methionine-deficient medium plus 20 μCi/ml of Tran[$^{35}$S]-label prior to lysis. WI-38 and HeLa S3 cells were lysed in 0.4 ml of lysis buffer per 100 mm plate. Lysates were cleared by centrifugation at 14,000 g for 15 min, adjusted to 10% glycerol, frozen in liquid nitrogen, and stored at −80° C. Cell lysates (1 mg) were incubated with 50 μl of antibody-coupled beads (1:1 suspension in lysis buffer) for 2 hr at 4° C. Precipitates were washed five times with 1 ml of lysis buffer and analyzed by SDS-PAGE followed by Western blotting or autoradiography. Western blotting was performed as described (Harlow, E., & Lane, D., *Antibodies: A Laboratory Manual*, Cold Spring Harbor Laboratory, Cold Spring Harbor, N.Y., 1988). $^{PHis6}$hCUL1 and $^{HA}$hSKP1 were detected by rabbit polyclonal anti-hCUL1 and biotinylated anti-HA (12 CA5) primary antibodies and visualized by incubation with goat anti-rabbit-HRP and streptavidin-HRP conjugates, followed by ECL detection (Amersham).

Ubiquitination reactions. Crude Sf9 cell lysates (500 μg) prepared from cells infected with $^{Phis6}$hCUL1 baculovirus were incubated with 20 μl anti-Polyoma beads for 2 hr at 4° C. to allow $^{Phis6}$hCUL1 binding. Beads were washed three times with lysis buffer and incubated with 1 mg of crude HeLa S3 lysate overnight at 4° C. Beads were then washed three times with lysis buffer and supplemented with 6 μg biotinylated ubiquitin (BUb), 500 ng hCDC34, 25 ng $^{His6}$yUBA1, 1 μl of 10×ATP-regenerating system (Feldman, R. M. R., et al., *Cell* 91:221–230, 1997), 1μl of 10×reaction buffer (Feldman et al., 1997, supra), and 0.5 μM ubiquitin aldehyde. Reactions were adjusted to 10 μl by adding 20 mM HEPES [pH 7.6], 100 mM KOAc, 1 mM DTT, incubated for 90 min at 30° C., and terminated by adding Laemmli sample buffer. Samples were analyzed by Western blotting with streptavidin-HRP conjugate. All ubiquitination reactions with chimeric SCF complexes were performed as described (Feldman et al., 1997, supra).

Example 2

Human CUL1 and its Interaction with hSKP1

To identify human proteins that interact with hCUL1 a two-hybrid screen was performed (Gyuris, J., et al., *Cell* 75:791–803, 1993; Fields, S., & Song, O., *Nature* 340:245–246, 1989). A fall length hCUL1 cDNA, fused to the LexA DNA-binding domain, was used as a bait to identify cDNAs from a HeLa library that encode hCUL1 interactors. This screen yielded clones encoding hSKP1, Protein Phosphatase 2A (PP2A) catalytic subunit, and the 20S proteasome subunit HsN3. None of these clones interacted with LexA-hCDK2 or LexA-Lamin C baits, suggesting that their interaction with LexA-hCUL1 was specific. The interaction of hCUL1 with hSKP1 was examined in detail (see below).

The identification of hSKP1 as a hCUL1-interacting protein suggested that these proteins may be subunits of a complex in human cells that is similar to the SCF ubiquitin ligase of budding yeast. To test whether hCUL1 interacts with hSKP1 in vivo, affinity-purified rabbit polyclonal antibodies were prepared directed against the N- and C-termini of hCUL1. Both antibodies recognized one major polypeptide of ~80 kDa in transformed (HeLa S3) and nontransformed (WI-38) cell lines. This species comigrated with hCUL1 produced in Hi5 cells infected with a baculovirus that contains fall length hCUL1 cDNA. A more rapidly migrating species of recombinant hCUL1 detected in Hi5 cells by the anti-C-terminal antibodies presumably represents a breakdown product or initiation of translation downstream of the normal start codon, as this species was not detected by the anti-N-terminal antibodies. As expected, addition of a Polyoma antigen-hexahistidine tag to hCUL1 ($^{PHis6}$hCUL1) yielded a more slowly migrating hCUL1 band.

Neither polyclonal antibody precipitated hCUL1 from crude human cell lysates, precluding analysis of hCUL1 complexes in nontransfected cells. Thus, to evaluate the potential interaction of hCUL1 with hSKP1 in vivo, HeLa S3 cells were transfected with $^{PHis6}$hCUL1 and $^{HA}$hSKP1 expression vectors. Lysates were prepared from these cells 24 hr posttransfection and immunoprecipitated using cross-linked anti-Polyoma or anti-HA antibody beads. Proteins bound to the beads were separated by SDS-PAGE and analyzed by immunoblotting with anti-hCUL1 and anti-HA antibodies (FIG. 1B). Consistent with the two-hybrid data, hCUL1 was specifically detected in hSKP1 immunoprecipitates and vice versa.

Example 3

Human CUL1, HSKP1 and SKP2 Assemble into an SCF-LIKE Complex that can Associate with Cyclin A/CDK2 Kinase Human SKP1 was initially identified as a Cyclin A/CDK2-associated protein in transformed human cells (Zhang, H., et al., Cell 82:912–925, 1995). This association is mediated by SKP2, a human F-box protein with leucine-rich repeats, reminiscent of the GRR1 protein. CDC53 and ySKP1, together with the F-box protein GRR1, constitute a putative SCF ubiquitin ligase complex that targets G1 cyclins for degradation (Feldman, R. M. R., et al. Cell 91:221–230, 1997; Skowyra, D., Cell 91:209–219, 1997). The homology of human SKP1, SKP2, and hCUL1 proteins with components of the ySCF$^{GRR1}$ complex suggests that the human proteins may form a similar complex. This possibility was addressed by immunoprecipitating $^{PHis6}$CUL1 from [$^{35}$S]-labeled insect cells infected with baculoviruses that express $^{PHis6}$hCUL1, hSKP1, and SKP2; and by testing whether hCUL1 can assemble with a previously-described complex containing cyclin A/CDK2, hSKP1 and SKP2. The interaction of hCUL1 with the cyclin A/CDK2$^{HA}$/hSKP1/SKP2 complex was monitored by immunoprecipitating CDK2$^{HA}$ from [$^{35}$S]-labeled insect cells infected with all five viruses in various combinations. $^{PHis6}$hCUL1 efficiently assembled with hSKP1 and SKP2, suggesting that these proteins form a ternary complex similar to ySCF. Surprisingly, hCUL1 interacted with cyclin A/CDK2$^{HA}$ complexes in the absence of SKP2 or hSKP1 (note that hSKP1 does not associate with Cyclin A/CDK2$^{HA}$ complex in the absence of SKP2). This may be due to either a direct interaction between hCUL1 and cyclin A/CDK2$^{HA}$ or the presence of a bridging protein in insect cells (e.g., see Feldman, R. M. R., et al., Cell 91:221–230, 1997). Regardless, the ability of hCUL1 expressed in insect cells to assemble into complexes containing a cyclin-dependent kinase is likely to be physiologically significant, since $^{PHis6}$hCUL1 immunoprecipitates prepared from HeLa S3 cells contained histone H1 kinase activity.

Example 4

Human CUL1 Directly Interacts with HSKP1 and SKP2

The results described above suggest that hCUL1, hSKP1, and SKP2 can assemble into an SCF-like particle when co-expressed in insect cells. Due to the strong conservation of SCF components, however, these interactions might be mediated by other proteins provided by the host cells (for an example, see Feldman, R. M. R., et al. Cell 91:221–230, 1997). To test whether the observed interactions are direct, GST-hSKP1, GST-SKP2, and MBP-hCUL1 were produced in bacteria. The GST fusions (or unfused GST control) were mixed with MBP-hCUL1 or MBP and recovered by binding to GSH-Sepharose beads. Bound proteins were resolved by SDS-PAGE and visualized by Coomassie Blue staining. MBP-hCUL1, but not MBP, bound specifically and efficiently to GST-hSKP1 and GST-SKP2, but not GST. This result demonstrates that hCUL1 can bind to both hSKP1 and SKP2 without the participation of other proteins.

Example 5

Human CUL1 is Functionally Homologous to CDC53 and can form an Chimeric SCF Complex with YSKP1 and CDC4

The above observations indicate that hCUL1, the closest human homologue of CDC53, can assemble with hSKP1 and the F-box protein SKP2 into a complex reminiscent of the yeast SCF$^{GRR1}$ complex. This complex was next tested in the presence of hCDC34, E1 enzyme and ubiquitin to see if it was able to ubiquitinate proteins that either bind to it (cyclin A; Zhang, H., et al., Cell 82:912–925, 1995), are known to be degraded in S phase (cyclin E, E2 F-1; Won, K. A., and Reed, S. I., EMBO J. 15:4182–4193, 1996; Clurman, B. E., et al., Genes Dev. 10:1979–1990, 1996; Dynlacht, B. D., et al., Genes Dev. 8:17721786, 1994; Hofmann, F., et al., Genes Dev. 10:2949–2959, 1996), or have been implicated as substrates of hCDC34 (p27; Pagano, M., et al. Science 269:682–685, 1995; Sheaff, R. J., et al., Genes Dev. 11:1464–1478, 1997). These efforts were unsuccessful, raising the question of whether SCF$^{SKP2}$ complexes possess ubiquitin ligase activity. Moreover, ubiquitin ligase activity of the analogous yeast SCF$^{GRR1}$ complex has not been demonstrated yet, and might require additional unidentified components. However, whether hCUL1 is a functional component of a ubiquitin ligase complex genetically and biochemically was addressed by taking advantage of the considerable knowledge of this pathway in yeast. First, it was determined if hCUL1 can complement the cdc53$^{ts}$ mutation. hCUL1 and CDC53 were introduced under the control of the GAL1 promoter into a yeast strain carrying a temperature sensitive mutation in the CDC53 gene. Individual transformants were spotted at different dilutions on glucose (noninducing conditions, data not shown) and galactose (inducing conditions) media at permissive (24° C.) and restrictive (33° C.) temperatures. Only transformants that expressed wild type CDC53 or hCUL1 proteins were able to grow at the restrictive temperature. However, hCUL1 failed to complement a cdc53 null strain.

The ability of hCUL1 to complement the cdc53$^{ts}$ mutation implied that hCUL1 can assemble into functional SCF complexes with yeast proteins. To test this idea the interaction of hCUL1 with the budding yeast SCF subunits ySKP1 and CDC4 was examined. All three proteins were co-expressed in [$^{35}$S]-methionine-radiolabeled insect cells in various combinations. Human CUL1 specifically coprecipitated with ySKP1$^{HA}$ or $^{PHA}$CDC4/ySKP1, indicating that it can form a chimeric SCF$^{CDC4}$ complex with yeast proteins.

Previous findings identified SCF$^{CDC4}$ as a functional E3 that required the presence of all three subunits (CDC4, CDC53, and ySKP1) to catalyze ubiquitination of phosphorylated SIC1 (Feldman, R. M. R., et al., Cell 91:221–230, 1997; Skowyra, D., et al. Cell 91:209219, 1997). Preceding its ubiquitination, phosphorylated SIC1 is recruited to SCF$^{CDC4}$ by binding to the CDC4/ySKP1 substrate receptor (Feldman et al., 1997, supra; Skowyra, 1997, supra). Given that hCUL1 and hSKP1 assembled with CDC4 (FIG. 5B), it was tested as to whether these hybrid SCF complexes were able to promote ubiquitination of phosphorylated SIC1. Purified chimeric SCF complexes were incubated with MBP-SIC1$^{MHis6}$ and purified ubiquitination components. In the presence of SCF$^{CDC4}$, MBP-SIC1$^{MHis6}$ efficiently converted to high molecular weight forms. Omission of either CDC4, CDC53, or ySKP1 resulted in no activity. Replacement of CDC53$_{PHA}$ with $^{PHis6}$hCUL1 resulted in an SCF complex with modest ubiquitination activity that was dependent upon both CDC4 and ySKP1. Additionally, an SCF complex containing both $^{PHis6}$hCUL1 and hSKP1 along with $^{PHA}$CDC4 was also able to catalyze ubiquitination of MBP-SIC1$^{MHis6}$. The conversion of MBP-SIC1 to high molecular weight forms by hybrid CDC4/hCUL1/hSKP1 complexes required both substrate phosphorylation and the presence of ubiquitin. Interestingly, co-expression of $^{PHA}$CDC4, CDC53$_{PHA}$, and hSKP1 did not result in a functional SCF complex.

CDC53 was previously shown to interact with yCDC34 (Willems, A. R., et al., Cell 86:453–463, 1996). Thus, it was presumed that an SCF complex containing hCUL1 would prefer to use hCDC34 as an E2 as opposed to yCDC34. However, SCF$^{CDC4}$ complexes containing $^{PHis6}$hCUL1 with either ySK1$^{His6}$ or hSKP1 appeared to work much more efficiently with yCDC34 than with hCDC34 serving as the E2. Although the basis for this preference is unclear, it is possible that there exist additional human CDC34-like E2s that interact preferentially with hCUL1-containing complexes. Alternatively, the F-box subunit and might also contribute to the specificity for a particular E2 (Lisztwan, J., et al., EMBO J. 17:368–383, 1998).

Example 6

Human CUL1 Assembles with Ubiquitination-Promoting Activities in Human Cell Extracts The data are consistent with hCUL1 functioning as a component of a ubiquitin ligase complex in human cells. Since ubiquitination activity was not detected using recombinant hCUL1/hSKP1/SKP2 complexes, an assay that would allow the identification of either substrates or cofactors of a hCUL1-dependent ubiquitination pathway was designed. $^{PHis6}$hCUL1 produced in insect cells in the presence or absence of hSKP1 plus SKP2 was bound to anti-Polyoma beads and incubated with crude HeLa S3 lysates to allow binding of other potential SCF components, regulators, and substrates. After washing away unbound proteins, E1, hCDC34, biotinylated ubiquitin, and an ATP-regenerating system were then added to the beads. Following an incubation, reactions were fractionated by SDS-PAGE, transferred to nitrocellulose, and blotted with streptavidin-HRP to detect ubiquitin conjugates. Whereas $^{PHis6}$hCUL1 or $^{PHis6}$hCUL1/hSKP1/SKP2 complexes isolated from insect cells exhibited little ubiquitination activity, a high molecular weight smear characteristic of ubiquitinated proteins appeared when these same components were preincubated with HeLa S3 lysate prior to the assay. In contrast, no signal was detected when naked polyoma beads were preincubated with HeLa S3 lysate. The appearance of slowly migrating biotinylated proteins depended on the addition of ubiquitin and ATP-regenerating system to the reaction, indicating that the high molecular weight smear was due to ubiquitination occurring during the in vitro incubation.

Multiple homologues of the ySKP1, CDC53, and F-box subunits of the SCF ubiquitin ligase complex have been identified (Zhang, H., et al., Cell 82:912–925, 1995; Bai, C., et al., Cell 86:263–274, 1996; Kipreos, E. T., et al., Cell 85:1–20, 1996; Mathias, N., et al., Mol. Cell. Biol. 16:6634–6643, 1996) and implicated in various cellular processes, including kinetochore function (Connelly, C., & Hieter, P., Cell 86:275–285, 1996; Kaplan, K. B., Cell 91:491–500, 1997), S-phase progression (Zhang, H., et al. Cell 82:912–925, 1995), exit from the cell cycle (Kipreos, E. T., et al. Cell 85:1–20, 1996), transcript elongation, regulation of hypoxia-inducible genes, and suppression of tumorigenesis (Pause, A., et al., Proc. Natl. Acad. Sci. USA 94:2156–2161, 1997; Lonergan, K. M., et al., Mol. Cell. Biol. 18(2), 732–741, 1988). Based on the close homology between hCUL1 and CDC53, it was determined that hCUL1 functions as part of an SCF-like ubiquitin ligase complex in human cells. A two-hybrid screen to identify proteins that interact with hCUL1 yielded hSKP1, suggesting that hCUL1 does indeed assemble into SCF-like complexes in human cells. Several other observations reported here support this hypothesis. First, hCUL1 associates with hSKP1 in transfected HeLa S3 cells. Second, hCUL1 assembles into complexes with both hSKP1 and the F-box protein SKP2 in vitro. Third, hCUL1 complements the growth defect of a cdc53$^{ts}$ mutant. Fourth, hCUL1 and hSKP1 can form chimeric SCF complexes with CDC4, and these complexes are able to ubiquitinate the SCF$^{CDC4}$ substrate SIC1 in vitro. Fifth, hCUL1 associates with ubiquitination-promoting activity in HeLa S3 cell lysate. Taken together, these data strongly suggest that hCUL1 is a subunit of an SCF-like E3 complex in human cells.

What are the candidate substrates for hCUL1-dependent ubiquitination in human cells? SIC1, CLN2, and FAR1 must be phosphorylated before they can be ubiquitinated by the budding yeast SCF/CDC34pathway (Feldman, R. M. R., et al., Cell 91:221–230, 1997; Skowyra, D., et al., Cell 91, 209–219, 1997; Henchoz, S., et al., Genes Dev. 11(22), 3046–3060, 1997). The stability of many mammalian regulatory proteins—including IκB, β-catenin, p27, Cyclin D, and Cyclin E—is known to be controlled by phosphorylation (Pagano, M., et al., Science 269:682–685, 1995; Sheaff, R. J., Genes Dev. 11:1464–1478, 1997; Won, K. A., and Reed, S. I., EMBO J. 15:4182–4193, 1996; Clurman, B. E., et al., Genes Dev. 10:1979–1990, 1996; Diehl, J. A., et al., Genes Dev. 11:957–972, 1997; Verma, I. M., et al., Genes Dev. 22:2723–2735, 1995; Aberle, H., et al., EMBO J. 16:3797–3804, 1997). SCF-associated Cyclin A might also be a substrate of the SCF$^{SKP2}$ pathway. This is less likely, though, since cyclin A is thought to be primarily destroyed via the APC/cyclosome pathway, and both cyclin A and SKP2 activities are essential for entry into S phase (Zhang, H., et al., Cell 82:912–925, 1995). Instead, the tight association of cyclin A/CDK2 with SCF subunits both in vivo and in vitro might reflect an efficient coupling between substrate phosphorylation and ubiquitination in transformed cells.

Example 7

To characterize the composition of SCF complexes in vivo, the complexes were purified via an epitope tag attached to the Cdc53 subunit. Analysis of the purified complexes revealed the presence of an additional ~17 kD polypeptide that did not correspond to Skp1, Cdc34, or any known F box protein including Cdc4. Mass spectrometric analysis of the 17 kD protein excised from an SDS-polyacrylamide gel revealed it to be HRT1p. The HRT1 gene (YOL133 w) was originally identified in a screen for genes whose high level expression inhibits transposition of the Ty3 transposon (Saccharomyces Genome Database, http://genome-www.stanford.edu/Saccharomyces/).

HRT1 has close relatives in Drosophila, C. elegans, and humans. However, no biochemical function has been reported for the HRT1 polypeptide, and it is unclear how it influences transposition. We have confirmed by immunological tests that HRT1p is indeed included in SCF complexes. In yeast the HRT1 gene is an essential gene; the morphology of germinated spores bearing a deleted copy of HRT1 resembles that of cells that are deficient in SCF activity. Thus, HRT1 may also be essential for SCF function in yeast. It is possible that yeast SCF complexes expressed in Sf9 insect cells from baculovirus vectors may assemble with endogenous insect HRT1. Therefore, HRT1p may be of additional importance in the activity of an SCF complex.

This assay can be readily adapted to test whether the related hCUL2–hCUL5 proteins also assemble into ubiquitin ligase complexes in human cells. Lastly, by converting either the chimeric SCF complex assay or the biotin-Ub-based assay to a microtiter plate format, it should be feasible to screen chemical libraries to identify compounds that modulate the activities of hSKP1 and hCUL1. Given its critical role in cell division in budding yeast, inhibitors of human SCF might be valuable compounds for the development of novel anticancer chemotherapeutics.

Although the invention has been described with reference to the presently preferred embodiment, it should be understood that various modifications can be made without departing from the spirit of the invention. Accordingly, the invention is limited only by the following claims.

What is claimed is:

1. A method of identifying a compound that affects an activity of a polypeptide subunit of a Skp1p/Cullin/F-box ubiquitin ligase (SCF) complex, said method comprising:
   (a) contacting a test sample comprising a chimeric SCF complex assembled from subunits derived from yeast or human and another species and an ubiquitin-conjugating enzyme (CDC34p) with a test compound under suitable conditions that allow the components to interact;
   (b) adding to the components of (a) an ubiquitin-activating enzyme E1, ubiquitin, adenosine triphosphate (ATP), and a SCF substrate; and
   (c) comparing the ubiquitination of said SCF substrate in the test sample to ubiquitination of said SCF substrate in a sample not contacted with said test compound, wherein the difference in ubiquitination of said SCF substrate in the test sample is indicative of the effect of said compound on said polypeptide subunits.

2. The method of claim 1, wherein said effect is stimulation.

3. The method of claim 1, wherein said effect is inhibition.

4. The method of claim 1, wherein said compound is an antibody.

5. The method of claim 4, wherein said antibody is a monoclonal antibody.

6. The method of claim 1, wherein said species is mammalian.

7. The method of claim 6, wherein said species is human.

8. The method of claim 1, wherein said CDC34p is selected from the group consisting of yeast CDC34p, mouse CDC34p and human CDC34p.

9. The method of claim 1, wherein said SCF complex comprises a CUL polypeptide (CUL1p).

10. The method of claim 1, wherein said subunits of a SCF complex comprises yeast CDC4p, human CUL1p, and yeast SKP1p polypeptide (SKP1).

11. The method of claim 1, wherein said subunits of a SCF comprises yeast F-box protein CDC4 (CDC4p), yeast CDC53 polypeptide (CDC53p), and yeast SKP1 protein (SKP1p), and said CDC34p is a human CDC34p.

12. The method of claim 1, wherein said subunits of a SCF complex comprises yeast CDC4p, human CUL1p, and a human SKP1p.

13. The method of claim 1, wherein said SCF substrate is cyclin-dependent protein kinase inhibitor SIC1p.

14. The method of claim 13, wherein said difference in ubiquitination of said SIC1p is measured by the mobility of SIC1p on an SDS-polyacrylamide gel.

15. The method of claim 13, wherein said SIC1p is a chimeric protein.

16. The method of claim 1, wherein said ubiquitin is a derivatized ubiquitin.

17. The method of claim 16, wherein said derivatized ubiquitin is selected from the group consisting of a $^{125}$I-ubiquitin, a fluorescent ubiquitin, glutathione-S-transferase ubiquitin, and a biotinylated ubiquitin.

18. A method for identifying a test compound that affects the ability of a CDC4p, a SKP1p, a CDC34p, and a CDC53p or a CUL1p to ubiquitinate a substrate, said method comprising:
   (a) contacting a test sample comprising CDC4p, a SKP1p, a CDC34p, and either a CDC53p or CUL1p, with said test compound under conditions suitable to allow the components to interact;
   (b) adding to the components of (a) an E1 enzyme, ubiquitin and ATP, and a substrate for ubiquitination;
   (c) comparing the ubiquitination of said substrate in the test sample to ubiquitination of said substrate in a sample not contacted with said test compound, wherein the difference in ubiquitination of said substrate in the test sample is indicative of the effect of said test compound on said CDC4p, said SKP1p, said CDC34p, or said either CDC53p or CUL1p.

19. The method of claim 18, wherein a member of the group consisting of said CDC4p, said CDC53p, said SKP1p, and said CDC34p is a mammalian polypeptide.

20. The method of claim 19, wherein a member of the group consisting of said CDC4p, said CDC53p, said SKP1p, and said CDC34p is a human polypeptide.

21. The method of claim 18, wherein said ubiquitin is a derivatized ubiquitin.

22. The method of claim 21, wherein said derivatized ubiquitin is selected from the group consisting of a $^{125}$I-ubiquitin, a fluorescent ubiquitin, glutathione-S-transferase ubiquitin, and a biotinylated ubiquitin.

23. The method of claim 18, wherein said substrate for ubiquitination is selected from the group consisting of SIC1p and a chimeric SIC1p.

24. The method of claim 18, wherein said test compound is an antibody.

25. The method of claim 24, wherein said antibody is a monoclonal antibody.

* * * * *